United States Patent [19]
Bautista

[11] Patent Number: 4,836,671
[45] Date of Patent: Jun. 6, 1989

[54] LOCATING DEVICE

[75] Inventor: Val Bautista, Spring Grove, Ill.

[73] Assignee: Charles Lescrenier, Wauwatosa, Wis.

[21] Appl. No.: 147,593

[22] Filed: Jan. 22, 1988

Related U.S. Application Data

[63] Continuation of Ser. No. 720,710, Apr. 8, 1985, abandoned.

[51] Int. Cl.<sup>4</sup> ............................ G01C 3/00; A61B 6/08; G03B 13/20
[52] U.S. Cl. ............................ 356/1; 250/491.1; 354/165; 356/154; 356/375; 356/397; 356/152; 378/206
[58] Field of Search ............... 356/152, 9, 140, 144, 356/143, 154, 375, 397–399; 250/491.1; 354/165; 378/205, 206

[56] References Cited

U.S. PATENT DOCUMENTS

| | | | |
|---|---|---|---|
| 2,887,586 | 5/1959 | Reininger | 378/206 |
| 4,246,486 | 3/1979 | Madsen | 378/206 |
| 4,494,874 | 1/1985 | Di Matteo et al. | 356/1 X |

FOREIGN PATENT DOCUMENTS 1021814 12/1952 France ..................... 378/206

Primary Examiner—Stephen C. Buczinski
Assistant Examiner—Linda J. Wallace
Attorney, Agent, or Firm—Andrus, Sceales, Starke & Sawail

[57] ABSTRACT

A device determines the location of a point, line, or plane in space with respect to an object along an axis of projection from the object. The device includes a beam generator coupled to the object and generating a plane of light containing the axis of projection of the object. Additionally, the beam generator generates a ray of light oriented at an angle to the axis of the projection so as to intercept the axis at the point in space to be located. The position of the axis of projection in the plane is marked, preferably, by a second beam generator generating a plane of light containing the axis of projection of the object and oriented at an angle to the first plane. The coincidence of the ray and marking of the axis of projection in the plane indicates that the point in space has been located with respect to the object. The second beam generator may also provide a ray of light intersecting the axis of projection at a point different than the first ray. This permits the determination of two spaced points along the axis of projection.

7 Claims, 7 Drawing Sheets

LOCATING DEVICE

The present application is a continuation of U.S. patent application 06/720,710, filed Apr. 8, 1985, and now abandoned.

The present invention relates to a device for determining the location of a point, line, or plane with respect to an object.

Many situations exist in which it is necessary to locate a point, line, or plane in space with respect to an object. A typical situation is in the field of radiography where it is necessary to know the location of an X-ray film cassette from an object such as an X-ray generator.

A standard method for locating a point, line, or plane in space typically involves measuring the distance to the location, as through a measuring device such as a ruler or tape measure. These methods, though effective, require moving from the object to the point in space to make the measurement. If a second position needs to be located in order to establish a line in space, the procedure must be repeated and some mechanical device must be erected to mark the two points in space determining the line. If a plane is to be located in space, three points must be located and marked. These necessities impose physical limitations and requirements on the locating procedure.

The present invention is directed to an improved locating device for locating a point, line or plane in space which overcomes the foregoing shortcomings of the prior art.

More specifically the present invention is directed to a device for determining the location of a point, line, or plane in space with respect to an object along an axis of projection from the object. In its simplest form utilized to determine a point in space, the device includes a beam generator coupled to the object and generating a plane of light containing the axis of projection of the object. Additionally, the beam generator generates a ray of light oriented at an angle to the axis of the projection so as to intercept the axis at the point in space to be located. The position of the axis of projection in the plane is marked by a second beam generator generating a plane of light containing the axis of projection of the object and oriented at an angle to the first plane The coincidence of the ray and the marking of the position of the axis of projection in the plane indicates that the point in space has been located with respect to the object.

In the application of the device to locating an X-ray film cassette with respect to an X-ray source, one of the X-ray source or cassette is moved along the axis of projection until the coincidence is obtained. The X-ray film cassette is thus located at the point in space.

In a similar manner, the device can locate two points in space, and thus a line, on three points in space, and thus a plane.

The invention is further explained in the detailed description below, with the aid of the accompanying drawings in which.

Figure 1:
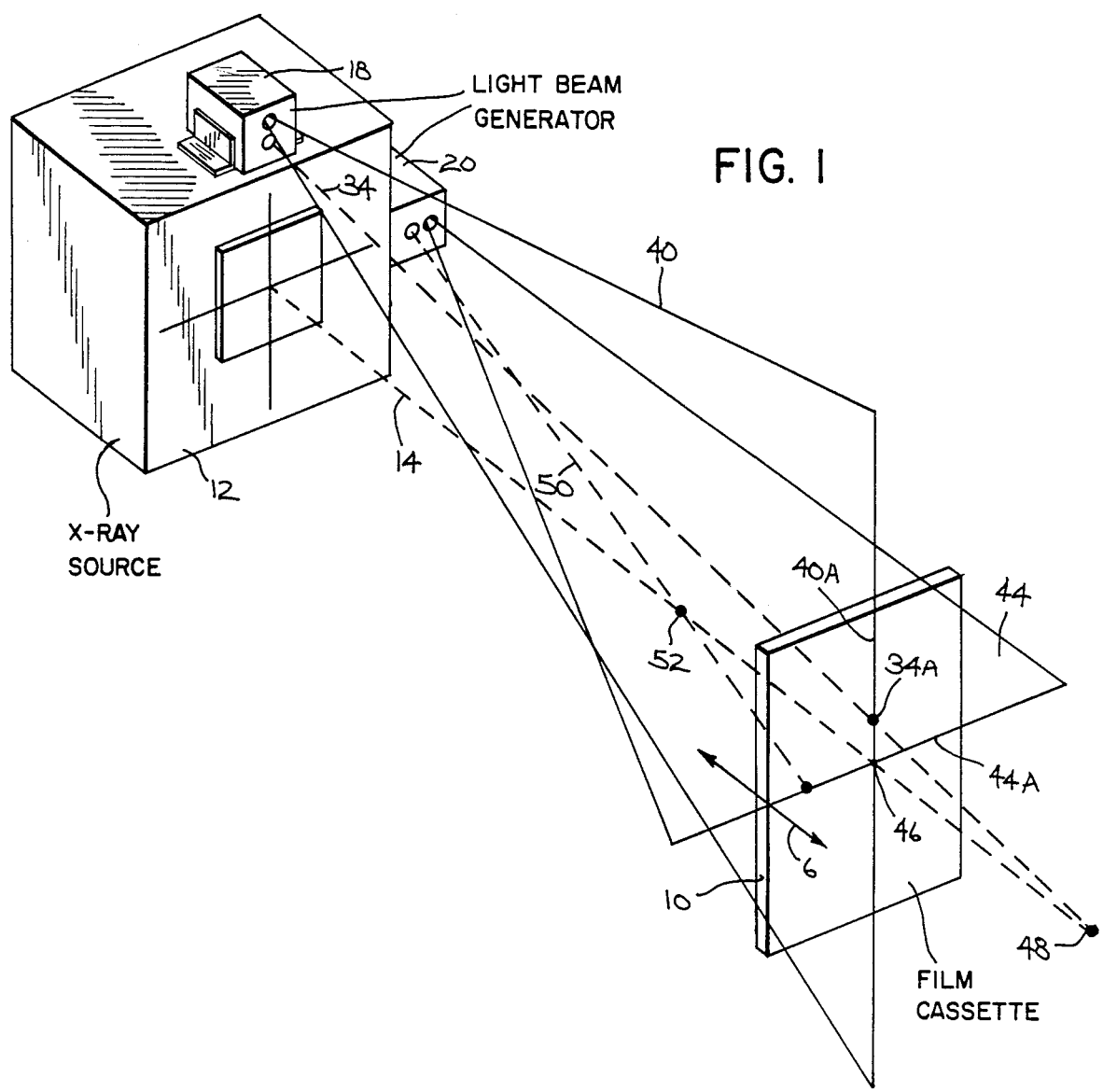
FIG. 1 is a perspective view of one embodiment of the locating device of the present invention suitable for use in locating a point or points in space.

FIG. 1 shows the locating device of the present invention employed to locate an X-ray film cassette 10 with respect to an X-ray source 12. The X-rays of source 12 are projected along axis 14. X-ray film cassette 10 lies generally normal to axis 4. One of X-ray film cassette 10 or X-ray source 12 is movable toward and away from the other along axis 14. In the following, X-ray film cassette 10 is described as movable toward and away from X-ray source 12, as indicated by arrow 16.

A pair of output heads or light beam generators 18 and 20 are placed on X-ray source 12. Beam generators 18 and 20 may be identical in construction and one such beam generator 18 is shown in detail in FIG. 2. A source of light, such as a laser provides light to fiber optic cable 22. This is applied to focusing lens 24 mounted on housing 26 that focuses the light from cable 22 into a thin, generally circular ray 28. Ray 28 passes through a beam splitter 30 which may be formed as a half silvered mirror. The transmitted portion of ray 28 exits housing 26 through opening 32 as ray 34. The reflected portion of ray 28 is applied to mirror 36 and cylndrical lens 38. Cylindrical lens 38 spreads the ray into a plane of light 40 lying in the plane of the paper. Light plane 40 exits housing 26 through opening 42. Plane 40 and ray 34 may both be in the plane of the paper.

As shown in FIG. 1, beam generator 18 is mounted on top of X-ray source 12 so that light plane 40 is vertical and aligned with axis of projection 14. Beam generator 20 is mounted on the side of X-ray source 12 so that light plane 44 generated by beam 20 is horizontal and aligned with axis of projection 14. Light planes 40 and 44 thus form a cross, the intersection 46 of which marks axis 14. As such, beams 40 and 44 can be used to center X-ray film cassette 10 on axis 14 and the X-rays from X-ray source 12.

Figure 2:
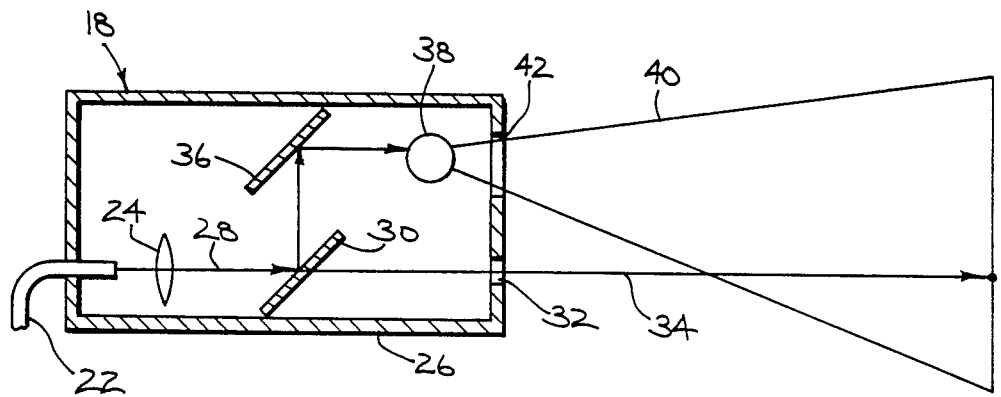
FIG. 2 is a cross sectional view of a light beam generator used in the locating device.

As shown in FIG. 2, ray 34 is projected from beam generator 18 at an angle to axis 14 to intersect the axis at point 48 to be located in space.

Figure 3:
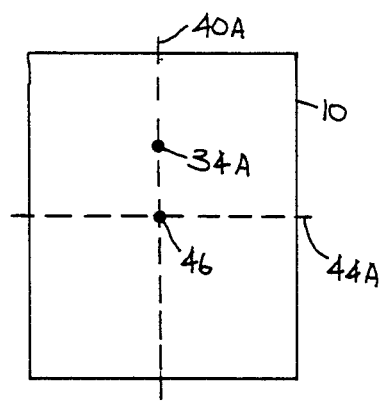
FIGS. 3 and 3A shows a projection of light planes and light rays by the device of FIG. 1 on a planar member in one position.

FIG. 3 shows the face of X-ray film cassette 10 facing X-ray source 12 and receiving the beams of light from beam generators 18 and 20. As noted above, the line projections 40-A and 44-A of light planes 40 and 44, respectively, form a cross, the intersection 46 of which lies on axis 14. Ray 34 appears as dot 34-A removed from the intersection of planes 40 and 42. Planes 40 and 44 need not intersect at 90° unless so desired. While the intersection of planes 40 and 44 is used to mark axis 14, some other means, such as a marker on cassette 10 may also be utilized.

Figure 3A:
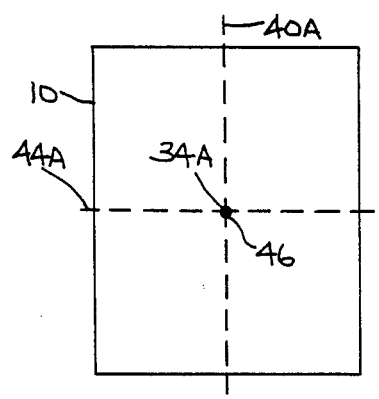

As X-ray film cassette 10 is moved away from X-ray source 12 along axis 14, dot 34-A moves toward intersection 46. When X-ray film cassette 10 has reached point 48 on axis 14, dot 34-A will coincide with intersection 46, as shown in FIG. 3A. Point 48 is thus located in space along axis 14 and X-ray film cassette 10 is positioned at that point with respect to X-ray source 12.

The position of point 48 on axis 14 may be determined by the tilt of beam generator 18 and ray 34 with respect to axis 14.

It may also be desired to determine the location of two points in space along axis 14. For example, it may be desirable to locate the maximum and minimum limits of travel of X-ray film cassette 10 with respect to X-ray source 12. Or it may be desired to locate X-ray film cassette 10 at locations established by radiological standards. For this purpose, beam generator 20 may provide a ray of light 50 intersecting axis 14 at the second point 52 to be located. Ray 50 may lie in the plane 44 of beam generator 20.

Figure 4:
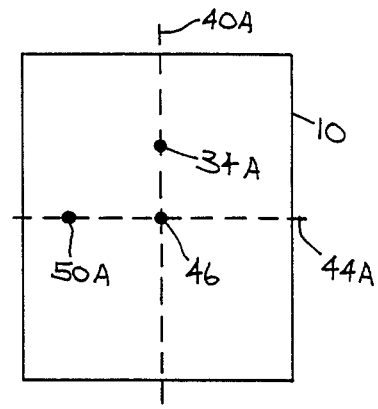
FIG. 4, 4A and 4B are views similar to FIG. 3 but showing the projection of light planes and rays on a planar member in different positions.
Figure 4A:
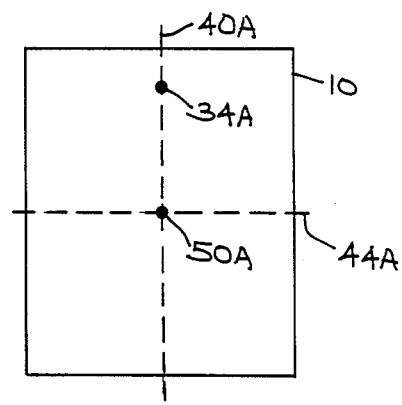

The operation of the locating device with rays 34 and 50 is shown in FIG. 4. FIG. 4 shows the light planes and rays applied to X-ray film cassette 10 when it is in the position shown in FIG. 1. Light planes 40 and 44 provide line projections 40-A and 44-A crossing at intersection 46 on axis 14. Ray 50 forms dot 50-A on line projection 44-A. Ray 34 forms dot 34-A on line projection 44-A. As X-ray film cassette 10 is moved towards X-ray source 12, dot 50-A will move along line 44-A toward intersection 46. Dot 34-A will move away from intersection 46. When cassette 10 reaches point 52, dot 50-A will coincide with intersection 46, as shown in FIG. 4A.

Figure 4B:
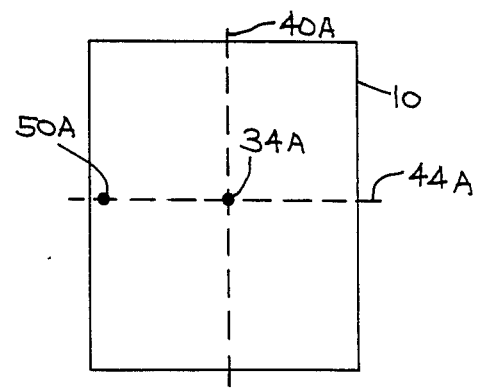

When film cassette 10 moves away from X-ray source 12 dot 34A will approach intersection 46 along line 40-A, reaching it when X-ray film cassette 10 is located at point 48, as shown in FIG. 4B.

The maximum and mimimum locations of film cassette 10 can thus be established by monitoring the movement of one or the other of dots 34A or 50-A on the respective lines 40-A or 44-A on the side of cassette 10 facing X-ray source 12.

Figure 5:
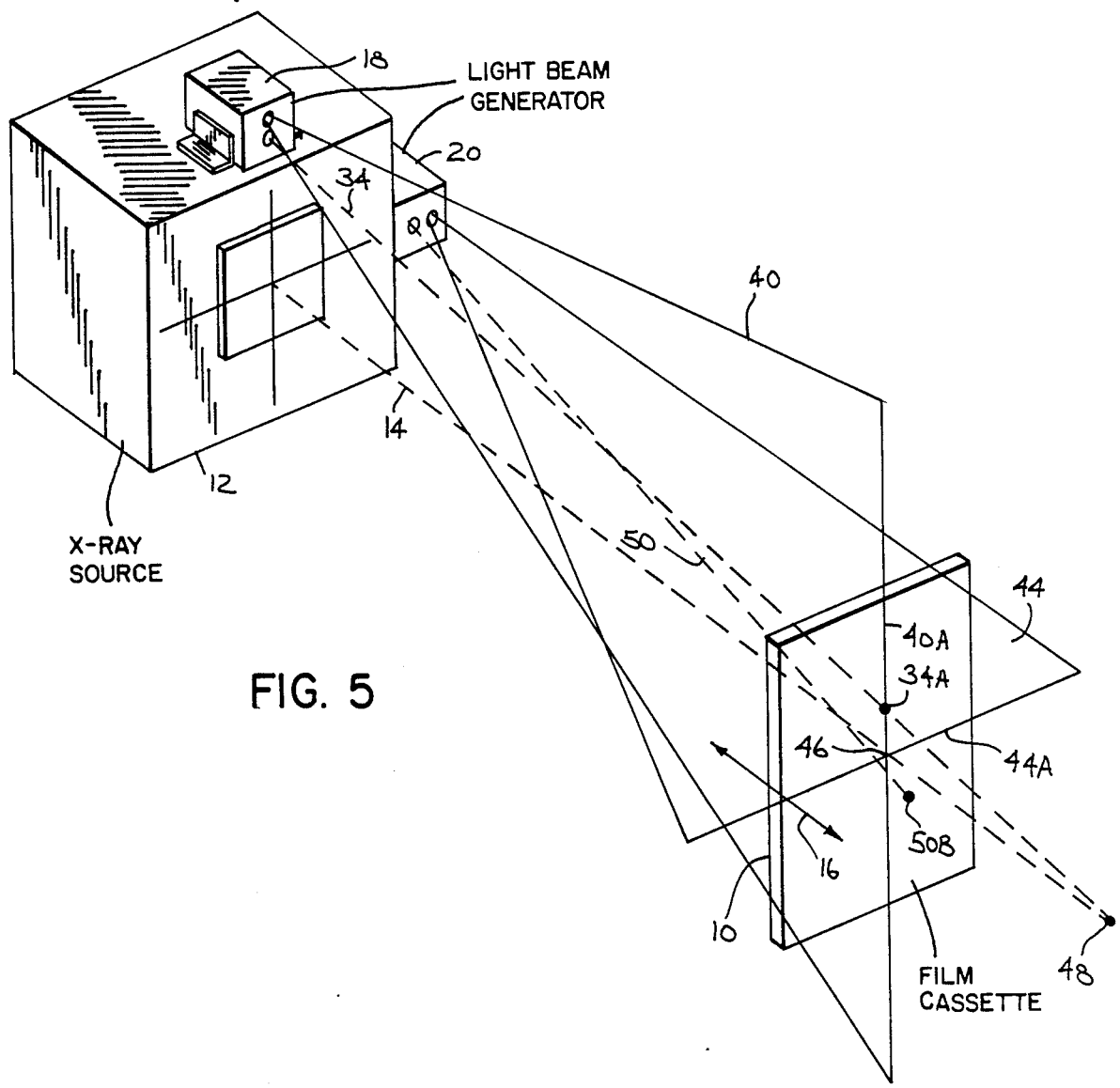
FIG. 5 is a perspective view similar to FIG. 1 showing another embodiment of the present invention.
Figure 6:
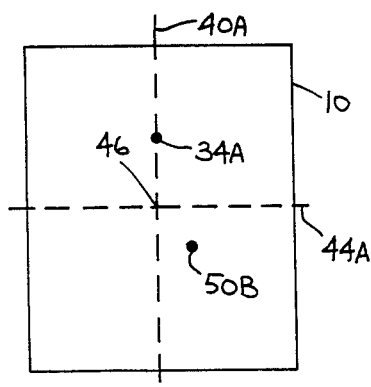
FIGS. 6 and 6A show the projection of light patterns by the device of FIG. 5 on a planar member in different positions.

FIG. 5 illustrates another embodiment of the invention in which the locating device can be used to determine the location of a line on a planar member in space. Instead of rays 34 and 50 lying in planes of light planes 40 and 44, one of beam generators 18 or 20 is adjusted so that the ray is out of the plane, as shown in FIG. 5. Ray 50 has been moved out of the plane of light plane 44. FIG. 6 shows the face of X-ray film cassette 10 in the same manner as FIGS. 3 and 4. Ray 50 is oriented so that it does not intersect plane 44-A within the limits of travel of X-ray film cassette 10 and provides dot 50-B. Ray 50 may be so oriented by a mirror, lens, or other means in the beam generator.

Figure 6A:
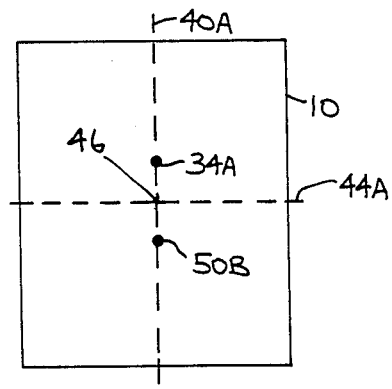

In the embodiment shown in FIGS. 5 and 6, as X-ray film cassette 10 is moved away from X-ray source 12, dot 34-A will move toward line 44-A. Dot 50-B will move toward line 40-A. At some point, dot 34-A will coincide with line 44-A or dot 50-B will coincide wth line 40-A. For example, dot 50-B may coincide with line 40-A as shown in FIG. 6A. This determines the first point 52 in space as shown in FIG. 7.

Figure 7:
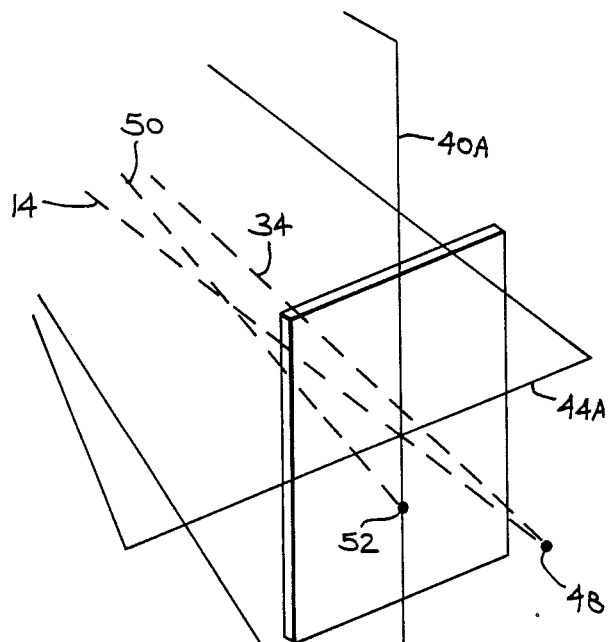
FIGS. 7 and 7A are partial perspective views taken from FIG. 5.
Figure 7A:
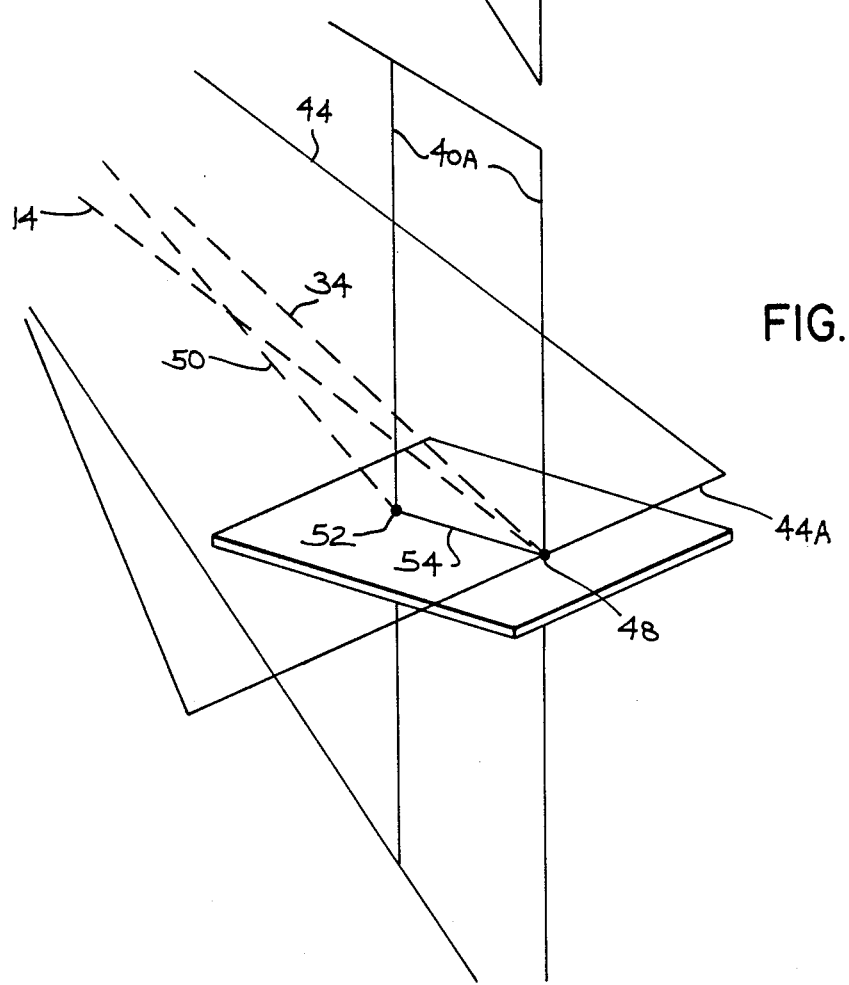

X-ray film cassette 10 is then rotated about an axis normal to axis of projection 14 and parallel to plane of cassette 10 at point 52, as shown in FIG. 7-A. Cassette 1 is rotated until dot 34-A coincides the intrsection of lines 40-A and 44-A at point 48 thereby to locate the second point on the line and thus line 54 itself.

While FIGS. 5, 6 and 7 show only one ray 50 moved out of plane 44, it will be appreciated that both rays can be moved out of their respective planes to appropriately locate a line in space. Film cassette 10 may be mounted in a gimbal means in addition to the appropriate orthogonal movement means in order to provide the necessary movements to cassette 10.

Figure 8:
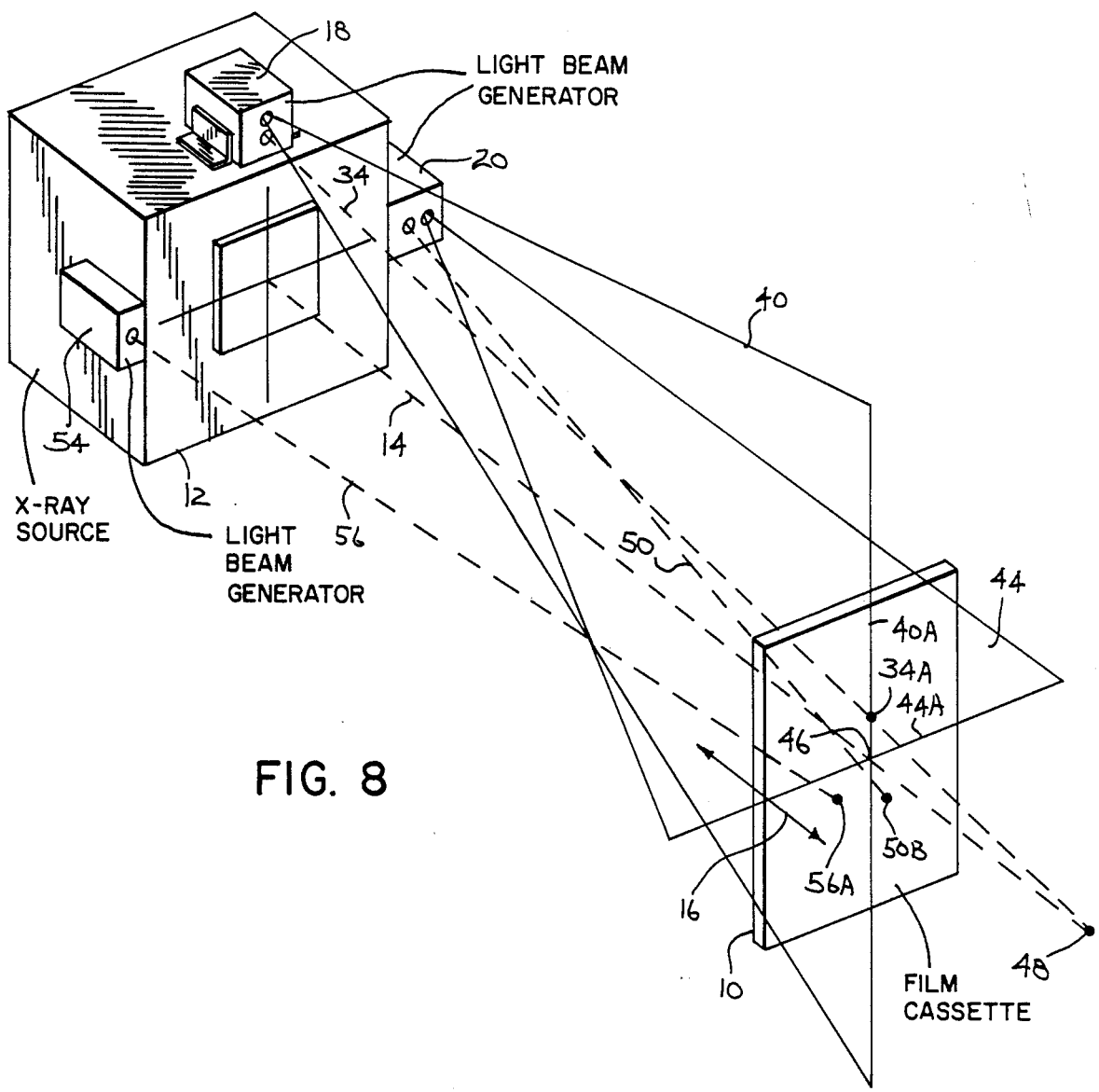
FIG. 8 is a perspective view similar to FIG. 1 showing another embodiment of the locating device of the present invention.
Figure 9:
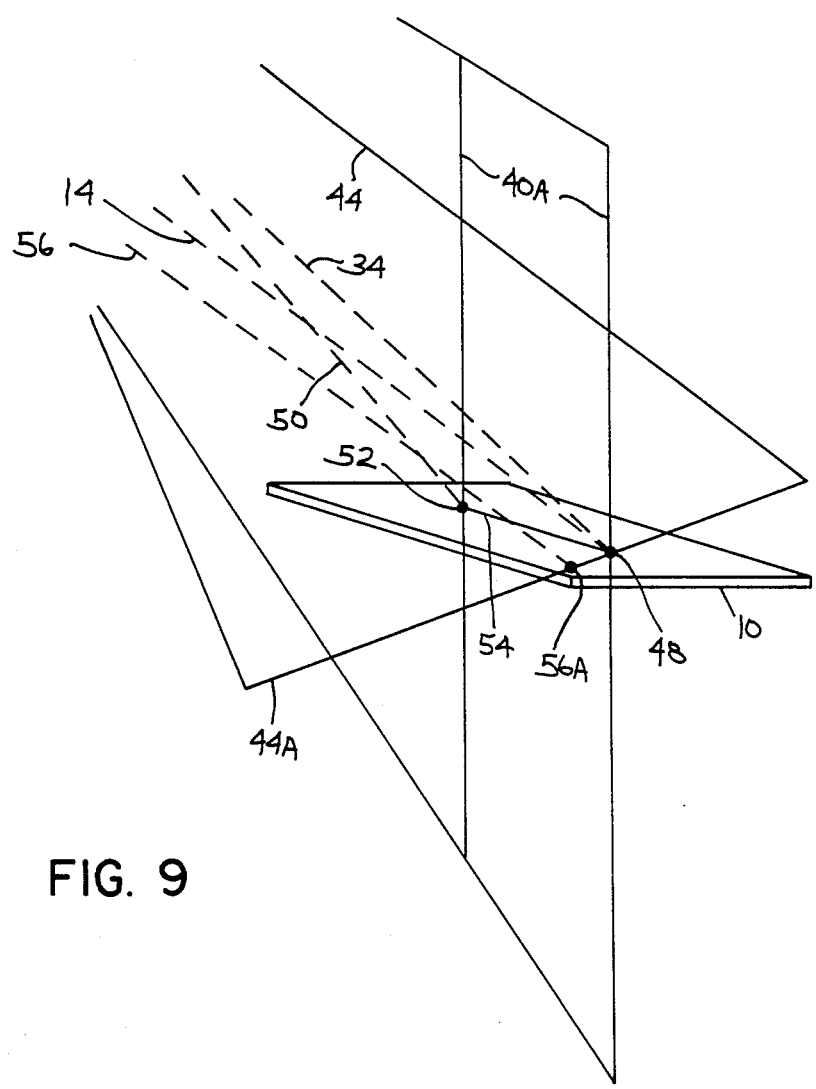
FIG. 9 is a partial perspective view similar to FIG. 7.

FIG. 8 shows an embodiment of the invention that can locate three points in space, thereby to define the plane of a planar member, such as X-ray film cassette 10. An additional beam generator 54 is placed on the side of X-ray source 12. Beam generator 54 provides ray 56, as shown in FIG. 8, and also in FIG. 9. Ray 56 lies at an angle to light plane 44.

The initial operation of the embodiment of FIG. 8 proceeds as described in connection with FIGS. 6 and 7. After the two points 48 and 52 have been located, film cassette 10 is rotated about the line 54 extending between points 48 and 52 until dot 56-A produced by ray 56 coincides with line projection 44-A of plane 44. The position of the plane of film cassette 10 is thus fixed in space.

Figure 10:
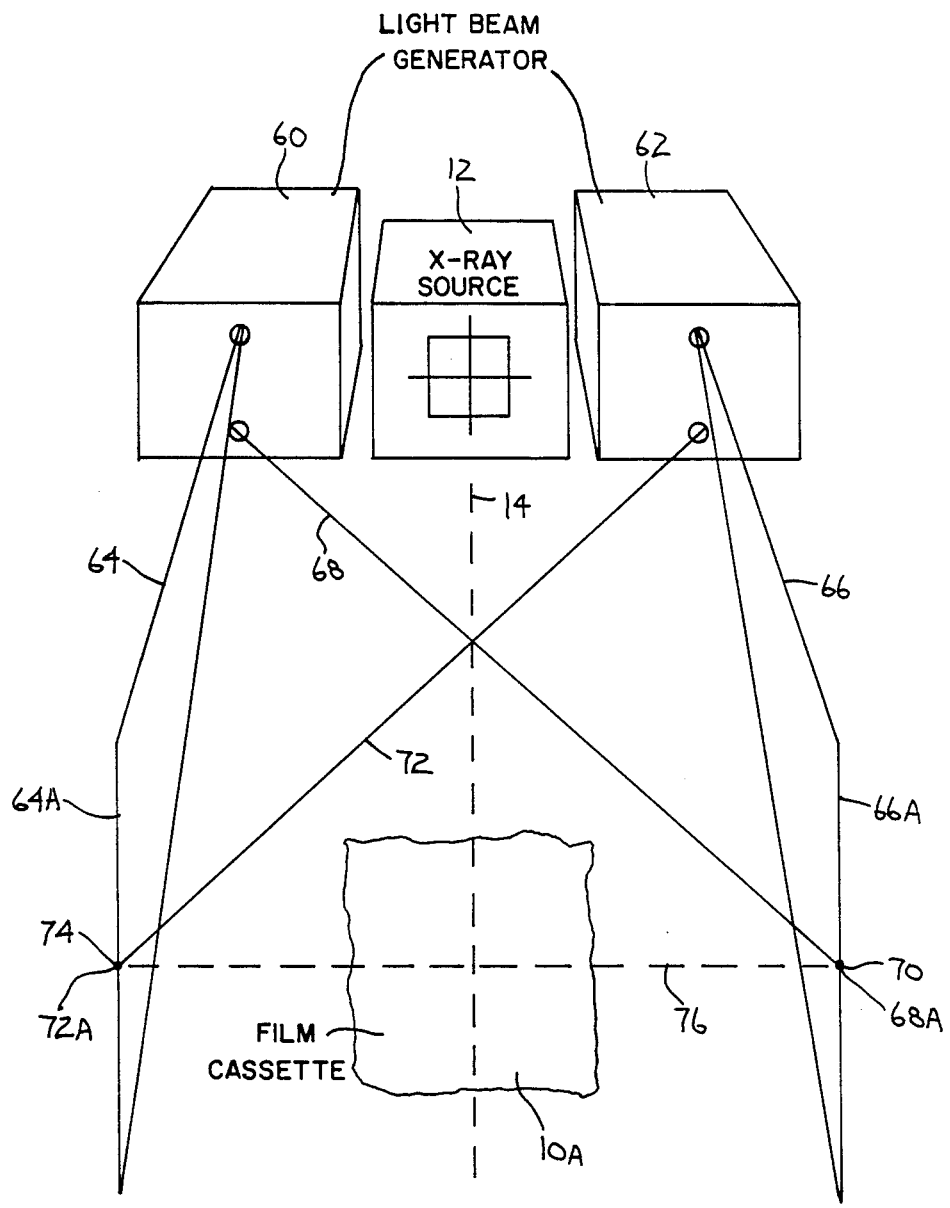
FIG. 10 is a perspective view of another embodiment of the locating device of the present invention.

FIG. 10 shows a further embodiment of the locating device of the present invention used to locate a line in space. In a typical application, it can be used to establish a line that is normal to axis of projection 14. In a radiological environment, this permits use of a film cassette 10 having a grid to reduce scatter and excessive fogging of the film. Unless film cassette 10 is normal to axis 14 along the direction of the grid, the X-ray picture is not achieved and may actually be cut off at the edges depending on how far and in what direction the cassette is rotated with respect to axis 14. The problem is particularly acute with portable X-ray units used at the bedside in hospitals. Once the cassette is placed on the bed or other convenient location, it is difficult or impossible to insure that the cassette is orthogonal with the X-ray beam emitted by X-ray source 12.

In the locating device of FIG. 10, a light beam generator 60 and 62 is provided on either side of X-ray source 12 and preferably laterally spaced with respect thereto. Beam generator 60 generates planar light beam 64 and beam generator 62 generates planar light beam 66. Planar light beams 64 and 66 are applied to film cassette 10-A. Beams 64 and 66 may be parallel, diverging, or converging, as desired or appropriate. Beam generator 60 also generates ray 68 that intersects planar light beam 66 produced by beam generator 62 at point 70. Beam generator 62 also generates light ray 72 that intersects planar light beam 64 produced by beam generator 60 at point 74. Points 70 and 74 are equidistant from X-ray source 12 so that line 76 extending between points 70 and 74 is normal to axis 14.

If X-ray film cassette 10-A is positioned so that dot 72-A produced by ray 72 on cassette 10 coincides with the line projection 64-A of planar light beam 64 and dot 68-A produced by ray 68 on cassette 10 coincides with the line projection 66-A of planar light beam 66, cassette 10 will be normal to axis 14 along one of its dimensions, thereby insuring that a grid cassette may be used without cutting off portions of the picture.

For other applications, the intersections of the planes and beams may be arranged so that the line between the points of intersection is other than normal to axis 14.

It will be appreciated by increasing the relative separation of the beam generators, such as beam generators 18 and 20 and 60 and 62, the accuracy and sensitivity of the locating device of the present invention can be increased.

Various modes of carrying out the invention are contemplated as being within the scope of the following claims particularly pointing out and distinctly claiming the subject matter which is regarded as the invention.

I claim:

1. A device for determining location of a point in space with respect to an object, the point lying on an axis of projection extending from the object, said device comprising:

a first generator means generating a first plane of light, said first generator means being located with respect to the object such that said first generator means is spaced from the axis of projection in a direction normal to the axis of projection, said plane of light containing the axis of projection of the object, said first generator means also generating a beam of light lying in said first plane of light, sad beam being visibly distinguishable from said first plane of light and oriented at an angle to the axis of projection so as to intercept the axis at the point in space to be located; and a second generator means generating a second plane of light, said second generator means being located with respect to the object such that said second generator means is spaced from the axis of projection in a direction normal to the axis of projection, said second plane of light containing the axis of projection, said second generator means being located with respect to said first generator means such that said second plane of light intersects said first plane of light at an angle, thereby to mark the position of the axis projection, the coincidence of the beam and whereby the intersection of said first and second planes of light indicates that the point in space has been located with respect to the object.

2. The locating device according to claim 1 further defined as a device for locating an X-ray film cassette with respect to an X-ray source providing X-rays along the axis of projection, said first and second generator means being further defined as located in a predetermined orientation with respect to the X-ray source and as applying said planes of light and said beam of light to said X-ray film cassette, whereby the coincidence of the beam and the intersection of said plane appears on the X-ray film cassette.

3. The locating device according to claim 1 further defined as locating a pair of points spaced along the axis of projection and wherein one of said generator means is further defined as generating a second beam of light lying in one of said planes of light, said second beam of light being visibly distinguishable from said planes of light and oriented at an angle to the axis of projection so as to intercept the axis at the second point in the space to be located.

4. The locating device according to claim 3 wherein said second generator means is further defined as generating said second beam of light.

5. The locating device according to claim 4 wherein said second generator means is further defined as generating said second beam of light in said second plane.

6. The locating device according to claim 1 wherein said first and second generator means are further defined as being so located with respect to the object and each other as to generate first and second planes of light intersecting at 90°.

7. The locating device according to claim 3 wherein said locating device is further defined as determining the location of an X-ray film cassette with respect to an X-ray source providing X-rays along the axis of projection, and wherein said first and second generator means are further defined as located in a predetermined orientation with respect to the X-ray source and as applying said first and second planes and beams of light to the X-ray film cassette.

* * * * *